United States Patent
Penno

(10) Patent No.: US 6,705,870 B2
(45) Date of Patent: Mar. 16, 2004

(54) PSYCHOMETRIC ASSESSMENT TESTING METHOD

(76) Inventor: Margaret B. Penno, 513 Murdock Rd., Baltimore, MD (US) 21212

( * ) Notice: Subject to any disclaimer, the term of this patent is extended or adjusted under 35 U.S.C. 154(b) by 0 days.

(21) Appl. No.: 09/944,438

(22) Filed: Aug. 31, 2001

(65) Prior Publication Data

US 2002/0061501 A1 May 23, 2002

Related U.S. Application Data

(60) Provisional application No. 60/231,355, filed on Sep. 8, 2000.

(51) Int. Cl.[7] ............................................. G09B 19/00
(52) U.S. Cl. .................... 434/258; 434/236; 273/153 R
(58) Field of Search ................................ 434/258, 238, 434/236, 237; 273/153 R

(56) References Cited

U.S. PATENT DOCUMENTS

| | | | | |
|---|---|---|---|---|
| 3,438,141 A | * | 4/1969 | Kirksey | 273/157 R |
| 3,811,203 A | * | 5/1974 | Mayfield | 273/157 R |
| 4,034,986 A | * | 7/1977 | Weidner | 273/236 |
| 4,950,167 A | * | 8/1990 | Harris | 434/322 |
| 5,520,393 A | * | 5/1996 | Rickey, Jr. | 273/237 |
| 5,979,895 A | * | 11/1999 | Dove | 273/157 R |
| 6,003,869 A | * | 12/1999 | Kuo | 273/259 |
| 6,193,234 B1 | * | 2/2001 | Jones | 273/157 R |
| 6,315,570 B1 | * | 11/2001 | Mathes | 434/237 |

* cited by examiner

Primary Examiner—Derris H. Banks
Assistant Examiner—Dmitry Suhol
(74) Attorney, Agent, or Firm—Law Offices of Royal W. Craig

(57) ABSTRACT

A method for psychometric assessment testing of both cognitive and motor ability to assimilate and follow instructions. The assessment method tasks a subject to assemble a subset of inter-fitting parts from a collection of parts in a specific manner as defined by an instruction set presented to the subject, and with the help of specific reference cues. A number of inter-fitting parts are placed before a subject, each bearing various labels for guiding assembly. Some of the parts are functionally similar except in dimension. Next, the subject is given a menu of the parts bearing not-to-scale illustrations of all the parts (labels omitted), and names for the respective parts. Next, the subject is given a ruler, and then a set of assembly instructions including a set of written directions for assembling a subset of the parts in a preselected manner by reference to part name, dimensions, and labeled indicia. The subject is instructed to begin, and an administrator times assembly. After completion, the administrator assesses the subject's aptitude by awarding points for properly assembling the subset of parts in the instructed manner, for steps taken by the subject during assembly, and for time to completion, the assessment thereby providing a measure of both cognitive ability and dexterity. The minimalistic content and sparse manner of delivering the instructions exercises the subject's ability to assimilate instructions on their own, as well as assimilating the apparent reference cues that he or she might need, thereby allowing full assessment of autonomy and self-orientation.

6 Claims, 7 Drawing Sheets

INSTRUCTIONS

1. Put end "L" of the 12 centimeter Rod into position 121 of the Connector Spool.

2. Place side "W" of the Bearing on end "R" of the 12 centimeter Rod.

3. Lay the completed work down horizontally with the green Bearing on the right.

INSTRUCTIONS

1. Put end "L" of the 14 centimeter Rod into position 121 of the Spinning Spool.

2. Place side "W" of the Bearing on end "R" of the 14 centimeter rod.

3. Lay the completed work down horizontally with the green Bearing on the left.

FIG. 9

PSYCHOMETRIC ASSESSMENT TESTING METHOD

CROSS-REFERENCE TO RELATED APPLICATIONS

The present application derives priority from U.S. provisional application No. 60/231,355 for "PSYCHOMETRIC ASSESSMENT TESTING METHOD"; filed Sep. 8, 2000.

BACKGROUND OF THE INVENTION

1. Field of the Invention

The present invention relates to assessment testing, and more particularly, to a psychometric assessment testing method for accurate and expedient measurement of the combined cognitive and motor ability to follow instructions.

2. Description of the Background

There are many assessment testing methods which try to provide an objective measure of mental ability independent of ethnic bias. These methods include simple pen and pencil psychometric ("IQ") tests (for example, the Stanford Binet and Wechsler). However, these standardized tests have come under increasing criticism because of their inherent biases. Specifically, these tests favor prior learning of: procedural strategies (such as the use of math tables enabling faster solutions, or how to approach other problems), and language (e.g., alphabet, vocabulary, colloquialisms). Over the past 20–30 years cognitive science has developed the theory that cognitive ability is based on the brain's information processing speed. This is due to studies that reveal high correlations between chronometric (reaction speed) cognitive tests such as Wonderlic, Ravens and WAIS, and brain-speed, as measured via neural conduction velocity (optic-nerve transmission speed). Thus, current thinking is that basic intelligence can be measured by assessing the elementary cognitive processes (ECPs) that are involved in every stage of cognition from perception through decision-making to reaction. ECPs are comprised of the following components: the perceptual registration ("apprehension") of the stimuli (bits of information); the identification ("discrimination") of the information; the "selection" and "encoding" of the information, and the appropriate reaction, be it: physical (sensory-motor), i.e., "simple" reaction-time (RT), or; cognitive, ie, "choice", "discrimination" and "decision" RTs. Cognitive reactions involve the additional ECPs of "rehearsal" and further "encoding" of appropriately selected information while memory files are accessed, followed by the "transformation" and "manipulation" of retrieved information for the purposes of making the appropriate choice, discrimination or decision response. Any test that challenges and quantifies elementary cognitive processes is referred to as an elementary cognitive task (ECT). A decision RT test requires the access of short term memory and/or long term memory (LTM) in order to render the correct "split-second" decision. For example, the stimulus may pair a word with a picture. The Rule might be, "If the word and picture are the same, press the right arrow key, otherwise press the left." The ideal mental ability test would exercise and quantify as many ECPs as possible. Indeed, test methods are evolving in this direction. However, most if not all are experimental rather than application oriented. In order to adapt the research to mass population measurement the following are (minimally) needed: (1) a comprehensive test approach that exercises most, if not all, of the known elementary cognitive processes, components and mechanisms of cognition, including: perceptual awareness, brain processing speed, cognitive processing (choice and decision) speeds, working memory capacity, and speed of long term memory (LTM) access (from episodic, semantic and/or symbolic divisions of LTM), and the subsequent speed and efficiency of working memory's organization of relevant data to make a correct choice or decision; and (2) a test approach as described above that can be administered and graded economically and expediently.

There remains a real and timely need for a practical way to assess the elementary cognitive processes underlying "intelligence" for purposes of screening and placement, and yet a fair way which is not influenced by culture or genetic history. An assessment approach capable of quantifying cognitive components as described above would be helpful in aiding educators and employers to better qualify and place individuals.

SUMMARY OF THE INVENTION

It is, therefore, an object of the present invention to provide a psychometric assessment testing method for accurate and expedient measurement of the combined cognitive and motor ability to follow instructions.

It is another object to provide an assessment testing method that is well-adapted to mass population testing due to its stunning simplicity (in terms of time investment and overhead).

It is another object to provide a comprehensive test approach that exercises most, if not all, of the known elementary cognitive processes, components and mechanisms of cognition, including; perceptual awareness, brain processing speed, cognitive processing (choice and decision) speeds, working memory capacity, and speed of long term memory (LTM) access (from episodic, semantic and/or symbolic divisions of LTM), and the subsequent speed and efficiency of working memory's organization of relevant data to make a correct choice or decision.

It is another object to provide an assessment testing method that offers a practical yet fair way to assess the elementary cognitive processes underlying "intelligence", and yet which is not influenced by culture or genetic history.

It is still another object to provide a robust and easily managed assessment testing approach capable of aiding educators and employers to better qualify and place individuals.

These and other objects are accomplished by the present invention, which is a method for psychometric assessment testing of both cognitive and motor ability to assimilate and follow instructions. The assessment method generally tasks a subject to assemble a subset of interfitting parts from a collection of parts in a specific manner as defined by an instruction set presented to the subject, and with the help of specific reference cues. More specifically, the assessment method accomplishes the above under a framework of three general provisions. The first is an orientation phase by which a subject is presented with a minimal instruction set including a combination of oral and written cues delivered in a particular manner according to script. The subject is also presented with reference cues that will serve as tools to help in accomplishing the task at hand. The minimalist content and sparse manner of delivering the instructions exercises the subject's ability to assimilate instructions on his or her own, as well as assimilating the apparent reference cues that he or she might need, thereby allowing full assessment of autonomy and self-orientation. The assessment method then elicits a second phase of strategy development by requiring the subject to map an approach to the problem using the assimilated instructions and appropriate reference cues at hand. A third phase is execution by which the subject applies the assimilated instructions and uses the assimilated reference cues to assemble the interfitting parts. However, the assessment framework provides a number of potential pitfalls that the subject must try to navigate. The potential pitfalls are cognitive hurdles that the subject must overcome. For example, the components use an overlapping numbering scheme that requires close attention to detail, the components are illustrated in reference cues but are not drawn to scale, thereby compelling use of a ruler for proper identification, etc. Each potential pitfall exercises an elementary cognitive task (ECT) and requires the access of short term memory and/or long term memory (LTM) in order to render the correct "split-second" decision, thereby testing both cognitive ability and dexterity as the subject manipulates the physical parts. Finally, the framework includes a closure phase which requires the subject to decide whether he or she has finished correctly or not, thereby allowing assessment of confidence in the result.

BRIEF DESCRIPTION OF THE DRAWINGS

Other objects, features, and advantages of the present invention will become more apparent from the following detailed description of the preferred embodiment and certain modifications thereof when taken together with the accompanying drawings in which:

FIG. 9 is a composite drawing of two exemplary instruction slips 90.

DETAILED DESCRIPTION OF THE PREFERRED EMBODIMENTS

The present invention is a robust psychometric test approach for assessing both cognitive and motor ability to assimilate and follow instructions. The assessment method generally tasks a subject to assemble a subset of interfitting parts from a collection of parts in a specific manner as defined by an instruction set presented to the subject, and with the help of specific reference cues. The particular design of the parts, content of the instructions, and the reference cues construct a testing framework that thoroughly exercises a subjects' cognitive and motor abilities in a matter of minutes and with very little overhead.

FIGS. 1–7 illustrate an exemplary set of color-coded interfitting component parts.

Figure 1:
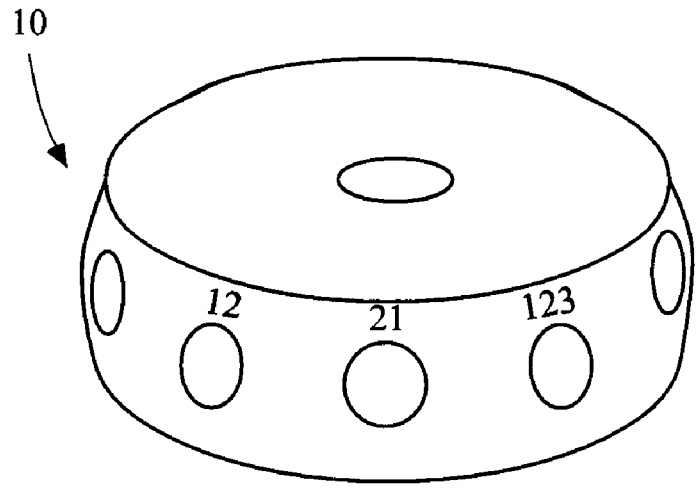
FIG. 1 is a perspective drawing of yellow connector spool 10.

FIG. 1 shows a yellow connector spool 10 having at least seven holes labeled with the following numbers: 121, 221, 212, 12, 21, 123, 122, and one unnumbered hole through the center.

Figure 2:
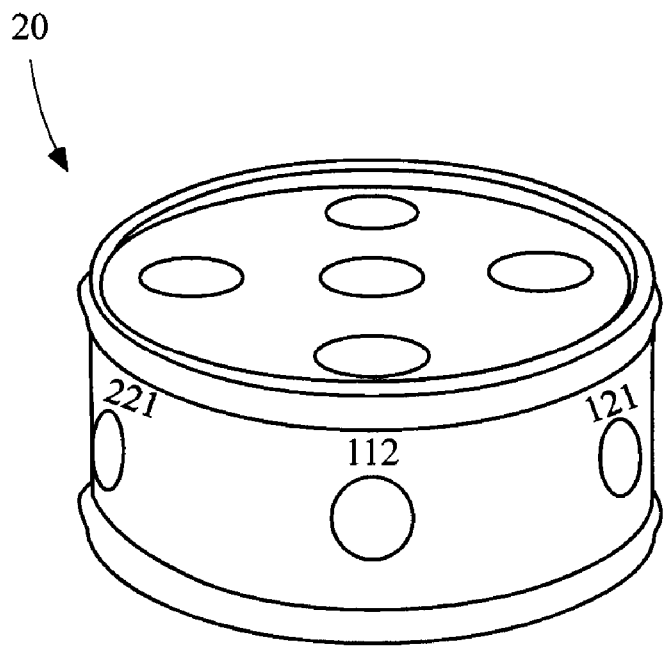
FIG. 2 is a perspective drawing of blue spinning spool 20.

FIG. 2 shows a blue spinning spool 20 having at least four holes labeled as follows: 121, 112, 221, 122, and five unnumbered holes through the center.

Figure 3:
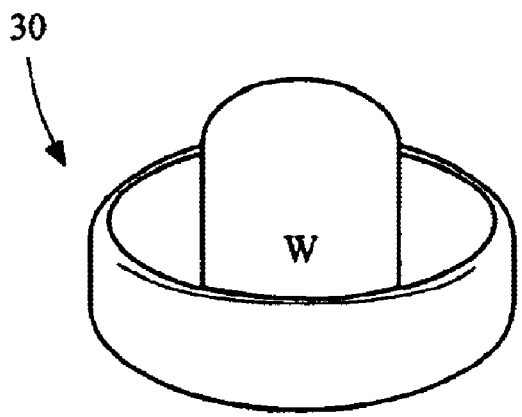
FIG. 3 is a perspective drawing of one of two orange caps 30.

FIG. 3 shows one of two orange caps 30 that are used, each marked with a "w" on the top surface.

Figure 4:
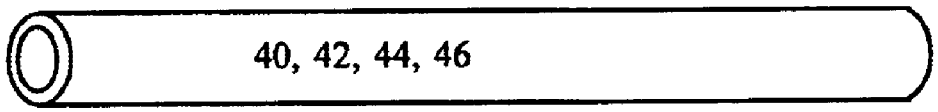
FIG. 4 is a perspective drawing of one of four connecting rods 40, 42, 44, 46.

FIG. 4 shows a plurality of connecting rods 40, 42, 44, 46 of different lengths and colors—all labeled with an "R" near one end and an "L" near the other. For example, a red 12 cm rod 40, blue 14 cm rod 42, green 7.5 cm rod 44, and purple 18.3 cm rod 46 are acceptable, all being of uniform diameter.

Figure 5:
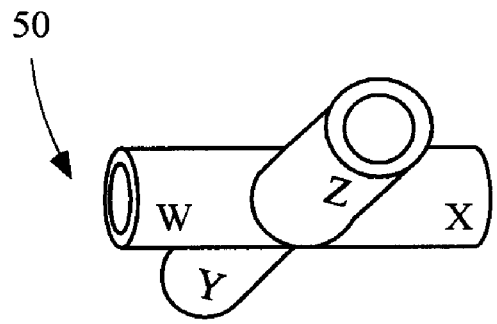
FIG. 5 is a perspective drawing of green bearing 50.

FIG. 5 shows a green bearing 50 with letters "w", "x", "y", and "z" labeled on each prong.

Figure 6:
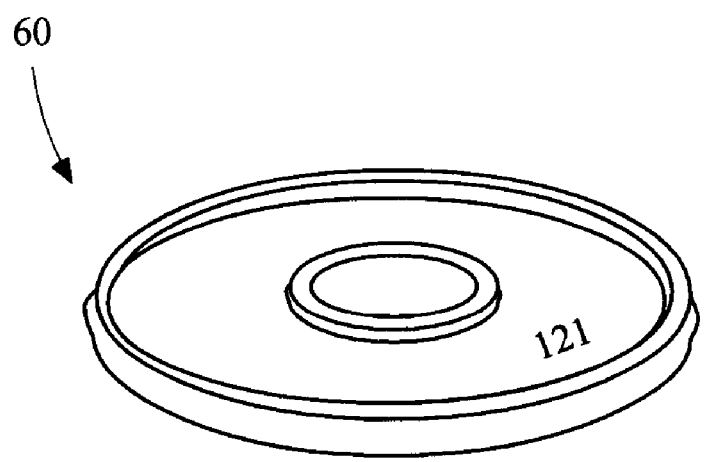
FIG. 6 shows an orange washer 60.

FIG. 6 shows an orange washer 60 labeled "121" on the surface.

Figure 7:
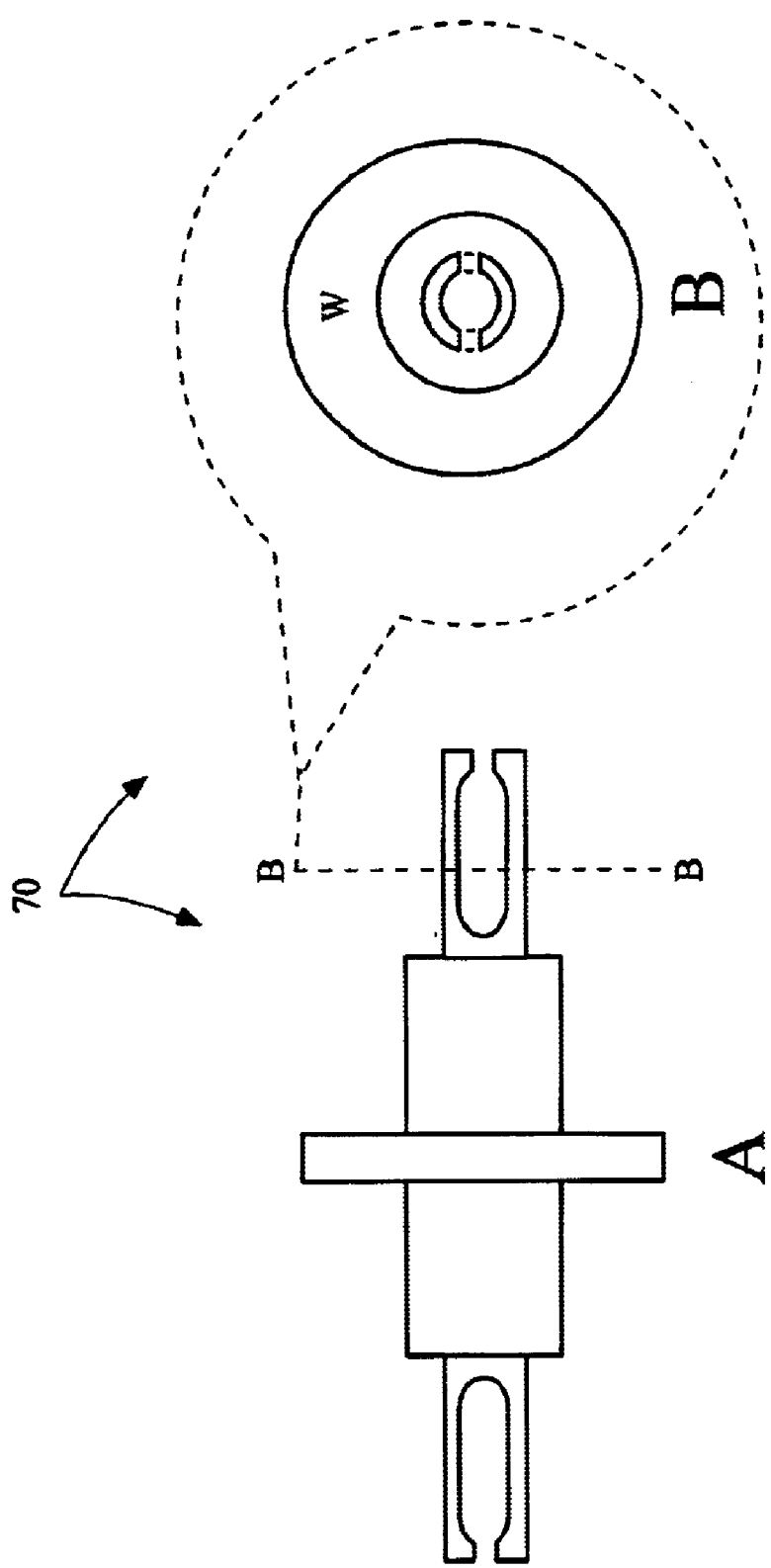
FIG. 7 shows one of two identical purple connectors 70.

FIG. 7 shows one of two identical purple connectors 70 having "w" marked on the surface.

The foregoing collectively comprise an exemplary set of components necessary for testing a subject's dexterity and cognitive abilities in accordance with the present method. In addition, the subject is provided with a conventional ruler delineated by metric (centimeters) on one side and inches on the other.

Figure 8:
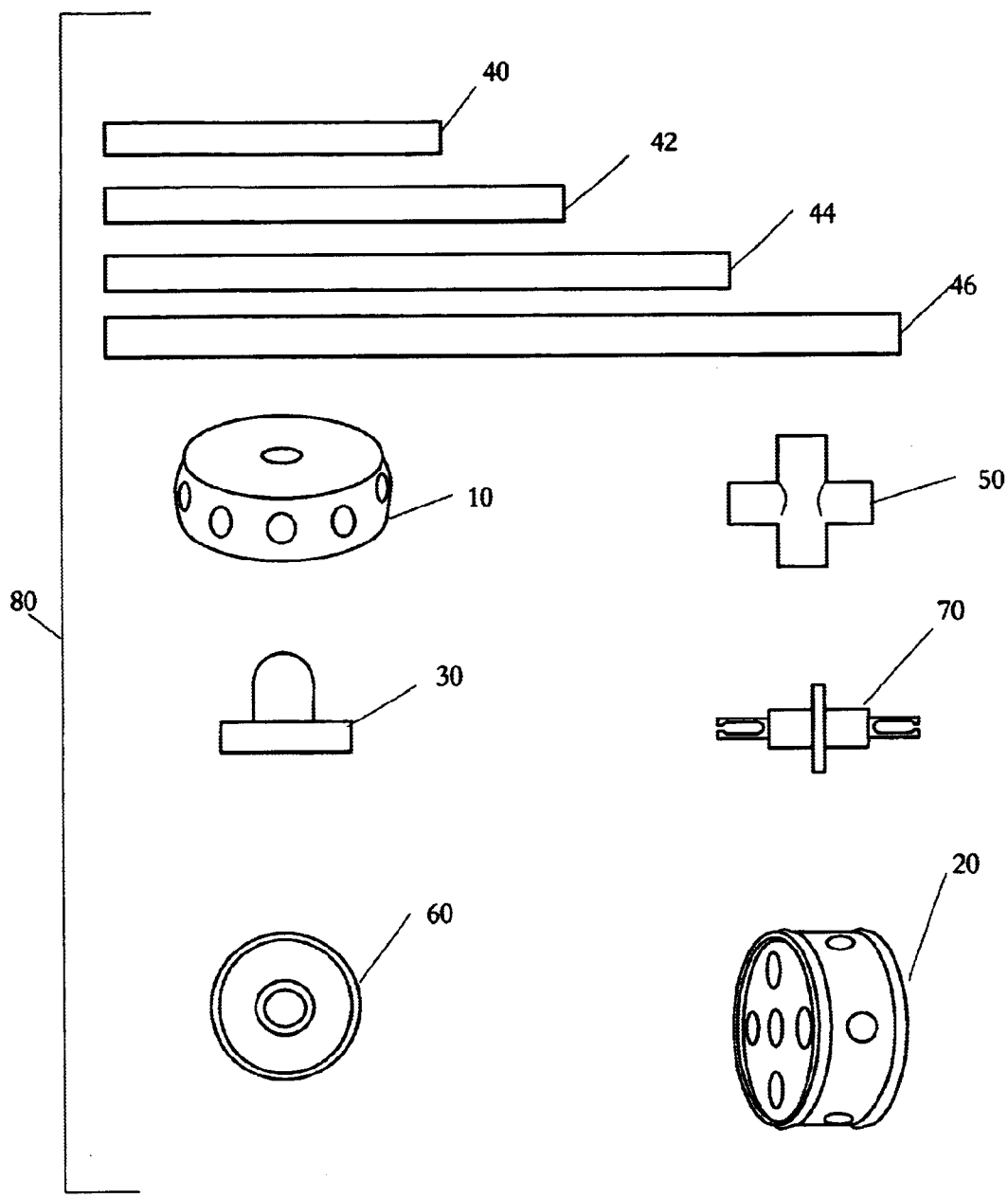
FIG. 8 is a front view of the illustrated menu 80 of the parts.

The subject is also presented with reference cues that will serve as tools to help in accomplishing the task at hand. Specifically, as shown in FIG. 8, the subject gets an illustrated menu 80 of the parts, not to scale, in color (to show the color of each part), and showing part name but not the letters or numbers actually marked on the parts. Thus, the series of red 12 cm rod 40, blue 14 cm rod 42, green 7.5 cm rod 44, and purple 18.3 cm rod 46 are as shown (in color) and all are generically labeled "rod." Likewise, the green bearing 50, orange washer 60, purple connector 70, orange cap 30 blue spinning spool 20, and yellow connector spool 10 are all generically labeled and shown in color.

As seen in FIG. 9, the subject is also given one of a plurality of instruction slips 90 (there may be a number of different printed instruction sets). A box is preferably included to hold all of the foregoing components. For the instructor's part, a standard interval timer is provided along with a camera for documentation and a score sheet for objective assessment.

Figure 10:
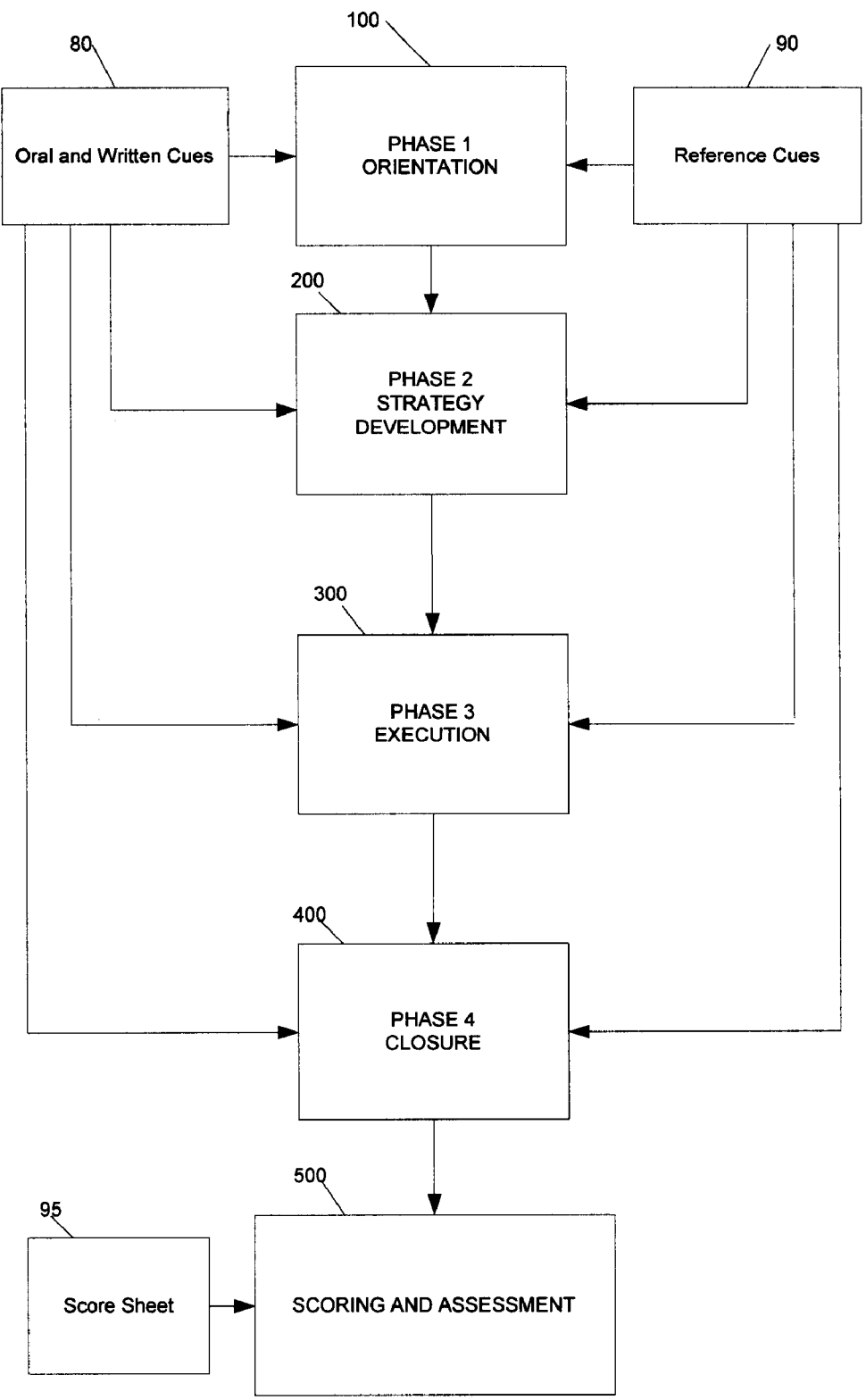
FIG. 10 is a flow diagram of the psychometric assessment method according to the present invention.

Given the foregoing components, FIG. 10 is a flow-chart depiction illustrating the method steps of the present invention. The assessment method of the present invention begins with an orientation phase at Step 100 by which a subject is presented with a minimal instruction set including a combination of oral and written cues 80 delivered in a particular manner according to script. The administrator's role is carefully crafted. For example, he or she must complete the following. Initially, the test materials must be out of sight. First, the administrator places the timer on the table, thereby conveying the time element of the test. Next, the box of parts is placed in front of the subject. The administrator says a scripted "Here are your parts". Next, the administrator places the menu of components 80 in front of the subject and says "Here is a picture of the parts" . . . "It is not to scale". Next, the administrator places the ruler in front of the subject and says "Here is your ruler". Finally, the administrator places one set of instructions in front of the subject and says "Here are your instructions" . . . "just follow the instructions" and "you may begin". The administrator then overtly presses START on the timer. The minimalistic content and sparse manner of delivering these instructions exercises the subject's ability to assimilate instructions on their own, as well as assimilating the apparent reference cues 90 that he or she might need, thereby allowing full assessment of autonomy and self-orientation.

The assessment method then elicits a second phase of strategy development at Step 200 by requiring the subject to map an approach to the problem using the assimilated instructions and appropriate reference cues at hand. Assuming that the subject has been given the first instruction set illustrated in FIG. 9, then the user must complete three concisely worded tasks . . .

1. Put end "L" of the 12 centimeter Rod into position 121 of the Connector Spool.
2. Place side "W" of the Bearing on end "R" of the 12 centimeter Rod.
3. Lay the completed work down horizontally with the green Bearing on the right.

After the subject reads the instruction set to the extent that he or she feels is appropriate to begin acting, the subject begins executing the instructions at step 300. Here the subject applies the assimilated instructions and uses the assimilated reference cues to assemble the inter-fitting parts. However, the assessment framework of the present invention belies a number of potential pitfalls that the subject must navigate. The potential pitfalls are cognitive hurdles that the subject must overcome. Each potential pitfall exercises an elementary cognitive task (ECT) and requires the access of short term memory and/or long term memory (LTM) in order to render the correct "split-second" decision, thereby testing both cognitive ability and dexterity as the subject manipulates the physical parts.

First, the instructions refer to the 12 centimeter Rod 40 and the subject must find it amongst the other components. If the subject listened and assimilated the administrator's admonition that the menu "is not to scale", he or she will proceed to measure the rods directly. Otherwise, time is wasted measuring pictures of the rods on the menu, or the wrong rod may be selected.

Next the subject must identify the Connector Spool 10 using the menu and retrieve same from the box. Once done, the subject must put end "L" of the 12 centimeter Rod 40 into position 121 of the Connector Spool 10. This tests attention to detail, because as previously mentioned the Connector Spool 10 has at least seven holes labeled with confusingly similar numbers: 121, 221, 212, 12, 21, 123, 122, as well as one hole through the center, unnumbered. All of the components use an overlapping numbering scheme that requires close attention to detail. Under time pressure the subject is prone to using the first familiar hole that he or she sees, and the others are ignored. The same potential pitfalls surface again in the second task, to place side "W" of the Bearing 50 on end "R" of the 12 centimeter Rod 40.

Finally, the subject is instructed to lay the completed work down horizontally with the green Bearing 50 on the right. This engenders the closure phase at Step 400 during which the subject will decide whether he or she has finished correctly or not, thereby allowing assessment of confidence in the result. When the subject finally does place the work down on the table, the administrator presses STOP on the timer. The administrator smiles and says, "Thank you", and when the subject leaves he or she scores the work. The administrator also takes a picture of the completed work with the instructions and score sheet used. Everything is put away and out of sight for the next client. The entire process is scripted for the administrator to ensure uniformity, inclusive of Responses to frequently asked questions. For example, the administrator is trained to respond as follows to the following questions:

Q. How much time do I have?
A. As much as you need.
Q. Can I do . . . (this or that)?
A. Everything you need is there.
Q. How did I do?
A. I am not at liberty to say.

In scoring the assessment test at Step 500, the administrator fills out a score sheet 95 to ensure objective assessment. The score sheet includes bibliographic information such as the subject's name, etc. Scoring employs a point system in which the subject is awarded or loses points for certain efforts. Points are allocated (or deducted) as follows.

Reads entire instructions first (1 point)
Uses Ruler (1 point)
Uses Picture (1 point)
Correct Parts (3 points)
Correct Positions (2 points)
Correct Orientation of Finished Work (1 point)
Correct Rod Orientation (1 point)
Finished in <2 minutes (1 point)
Reassembly (−1 point)

For screening purposes, an eight or above is considered to be a passing score.

A comments section is also provided for general comments.

Although the present system excels as a means for corporate and technical screening, it has broad application in other contexts.

Having now fully set forth the preferred embodiments and certain modifications of the concept underlying the present invention, various other embodiments as well as certain variations and modifications thereto may obviously occur to those skilled in the art upon becoming familiar with the underlying concept. It is to be understood, therefore, that the invention may be practiced otherwise than as specifically set forth herein.

I claim:

1. A method for psychometric assessment testing, comprising the steps of:
   placing a plurality of inter-fitting parts before a subject;
   placing a menu of said parts before the subject;
   placing a ruler before the subject;
   providing oral cues according to script;
   placing a set of assembly instructions before the subject and instructing them to follow the instructions;
   instructing the subject to begin;
   timing the subject during assembly;
   assessing the subject's aptitude by assessing points for their actions, including use of said ruler for properly identifying said parts, speed and success in assembly.

2. The method according to claim 1, wherein said inter-fitting parts bear labeled indicia for guiding the assembly of parts, and at least two of said parts are functionally similar except in dimension.

3. The method according to claim 1, wherein said menu bears off-scale illustrations of each of the plurality of parts omitting said labeled indicia, and said menu bears names of the respective parts proximating the illustrations, whereby similar functional parts bear the same name.

4. The method according to claim 1 wherein said assembly instructions comprise a set of written directions for assembling a subset of said parts in a selected manner according to part name, dimensions and labeled indicia.

5. The method according to claim 1 wherein said points are awarded for properly assembling the subset of parts in the instructed manner, and for steps taken by the subject during assembly, and for time to completion, the assessment thereby providing a measure of both cognitive ability and dexterity.

6. The method according to claim 1 wherein said points are awarded according to a pre-defined point system whereby points are added or subtracted based on the subject's actions.

* * * * *